United States Patent
Sternowski

(10) Patent No.: US 10,408,738 B1
(45) Date of Patent: Sep. 10, 2019

(54) NON-INVASIVE CORROSION DETECTION

(71) Applicant: Softronics, Ltd., Marion, IA (US)

(72) Inventor: Robert H. Sternowski, Cedar Rapids, IA (US)

(73) Assignee: Softronics, Ltd., Marion, IA (US)

( * ) Notice: Subject to any disclaimer, the term of this patent is extended or adjusted under 35 U.S.C. 154(b) by 166 days.

(21) Appl. No.: 15/190,817

(22) Filed: Jun. 23, 2016

Related U.S. Application Data

(60) Provisional application No. 62/186,038, filed on Jun. 29, 2015.

(51) Int. Cl.
*G01N 17/04* (2006.01)
*G01N 27/00* (2006.01)

(52) U.S. Cl.
CPC .......... *G01N 17/04* (2013.01); *G01N 27/00* (2013.01)

(58) Field of Classification Search
CPC .............................. G01N 17/04; G01N 27/00
USPC ........................................................ 324/701
See application file for complete search history.

(56) References Cited

U.S. PATENT DOCUMENTS

| | | | | |
|---|---|---|---|---|
| 7,282,928 | B1* | 10/2007 | Hladky ................. | G01N 17/02 204/404 |
| 2004/0149594 | A1* | 8/2004 | Eden ..................... | G01N 17/02 205/775.5 |
| 2009/0317075 | A1* | 12/2009 | Mandai ................. | H04B 10/60 398/25 |
| 2014/0254812 | A1* | 9/2014 | Quan .................... | H04R 29/00 381/58 |
| 2015/0268153 | A1* | 9/2015 | Johannes Jacobus Maria ........... | G01N 17/04 205/775.5 |
| 2015/0362423 | A1* | 12/2015 | Panossian ............. | F17D 5/08 324/700 |

* cited by examiner

*Primary Examiner* — Jeff W Natalini
(74) *Attorney, Agent, or Firm* — Shuttleworth & Ingersoll, PLC; Jason Sytsma

(57) ABSTRACT

A first signal generator for generating a first AC current signal and a second signal generator for generating a second AC current signal. A first combiner is coupled to the first signal generator and the second signal generator for combing the first AC current signal and the second AC current signal into a probe signal for applying directly to the unit under test. A receiver for detecting intermodulation distortion in the unit under test.

16 Claims, 2 Drawing Sheets

NON-INVASIVE CORROSION DETECTION

This application claims priority to U.S. Provisional Application No. 62/186,083 filed on Jun. 29, 2015, the contents of which are hereby incorporated by reference herein.

BACKGROUND

Disclosed is a system and method for non-invasive corrosion detection, and more specifically, detecting metal corrosion using Passive Inter-Modulation (PIM) generated by multi-tone radio signals flowing through galvanic corrosion junctions.

Corrosion is a significant problem for both military and commercial systems. Corrosion can cause structural failure of the corroded member. In electronic equipment, corrosion can distort or disrupt the electrical signal that propagates through a metallic connector, that is, a conductor susceptible to corrosion. Corrosion is also a significant source of Electromagnetic Interference that can disrupt nearby systems. Damaging levels of corrosion can be hard to detect because the corrosion may be inaccessible or imperceptible on visual inspection. The effect of corrosion on electrical transmission is generally not linear.

Periodic testing to detect and apply early structural corrosion prevention measures can provide an enormous safety and cost benefit. Unfortunately, highly reliable corrosion detection methods do not exist to allow inspection of complex closed structures, which are unique because they require extensive disassembly or destructive testing, both expensive and undesirable methods.

The prior art systems and methods are directed to inducing circulating currents in a unit under test (UUT) with an antenna generated electro-magnetic field. Another antenna is used to sense the response. The problem with such systems is that the EM field is not easily confined without expensive Faraday cages because the radiation propagates everywhere. Appropriately, the FCC regulates the use of such methods and systems, which add additional complexity and expense to the tests. Furthermore, such systems and methods are not precise given the width of a radiating antenna pattern. This means that it is time consuming to narrow down with any degree of precision the location of the corrosion.

Devising a means of detecting and locating corrosion via simple application of radio signals that flow through closed structures would be of enormous economic benefit.

SUMMARY

A system for detecting corrosion in a unit under test ("UUT") is disclosed. The system uses a pair of probes to directly inject a probe signal to the UUT and sense intermodulation distortion. The system comprises of a first signal generator for generating a first AC current signal and second signal generator for generating a second AC current signal. A first combiner is coupled to the first signal generator and the second signal generator for combing the first AC current signal and the second AC current signal into a probe signal for applying to the unit under test. A receiver detects intermodulation distortion ("IMD") in the UUT.

The system further comprises of a second combiner coupled to the first combiner for receiving the probe signal. Two probes are coupled to the second combiner. The two probes receive the probe signal and apply the probe signal to one of two distinct locations on the UUT. A step-down transformer is coupled between the two probes and the second combiner for stepping down approximately fifty ohm impedance on a second combiner side of the step-down transformer to lower impedance on the two probes side of the step-down transformer.

The system can comprise of a library of measurement tests on material similar to the unit under test and a comparator for comparing the IMD in the UUT with the measurement tests on the material similar to the UUT for determining an amount of corrosion in the UUT.

A method for detecting corrosion in the UUT is also disclosed. The method comprises of injecting a multi-tone probe signal to the UUT with a pair of probes and analyzing with a receiver an IMD signal sensed from the same pair of probes. The IMD signal is compared with a previously measured signal to determine the presence of corrosion. If no corrosion is detected, at least one probe of the pair of probes can be moved to another location on the UUT to continue testing. The previously measured signal can be representative of an IMD signal from a part similar to the UUT with an area of corrosion, or representative of an IMD signal from a part similar to the UUT without corrosion.

DETAILED DESCRIPTION

Figure 1:
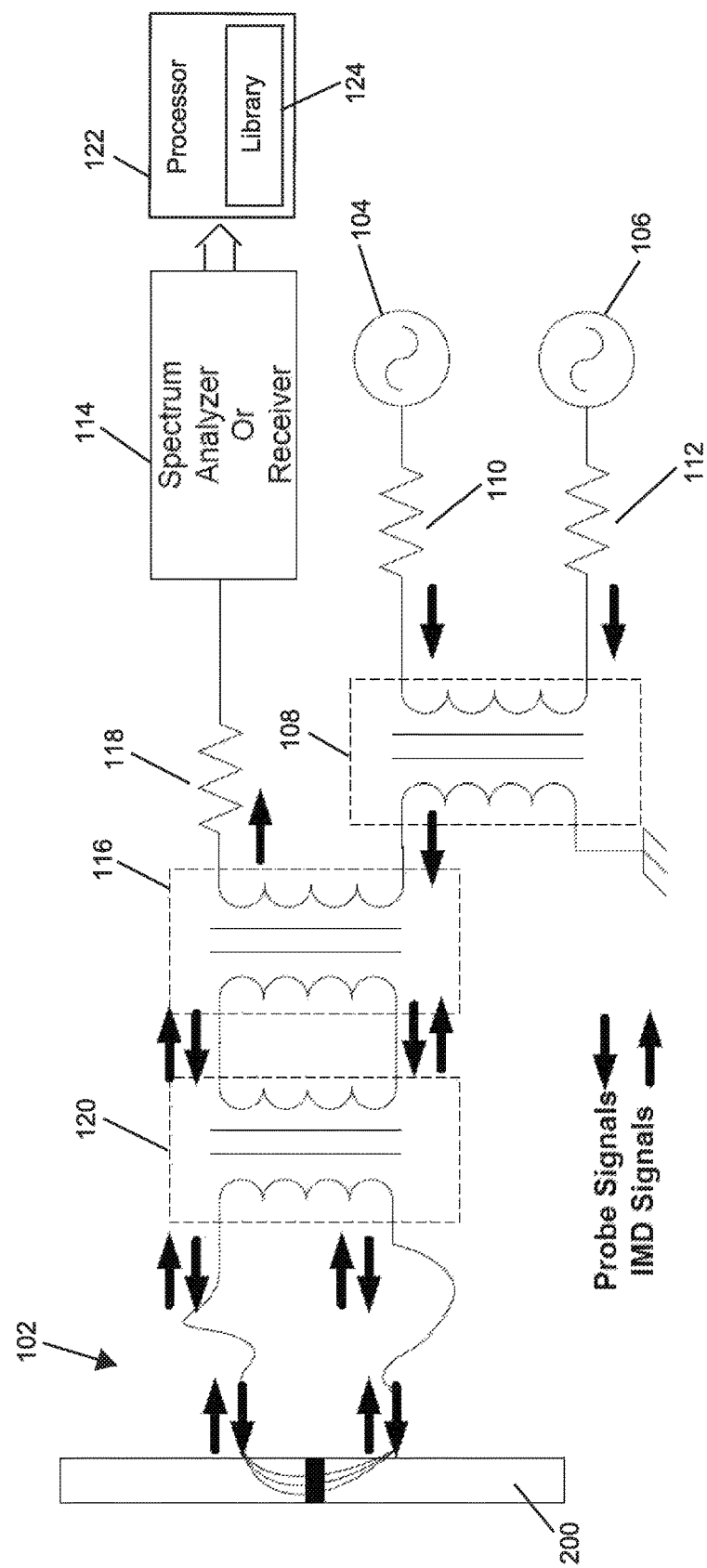
FIG. 1 is a diagram of a corrosion detection system in accordance with this disclosure.
Figure 2:
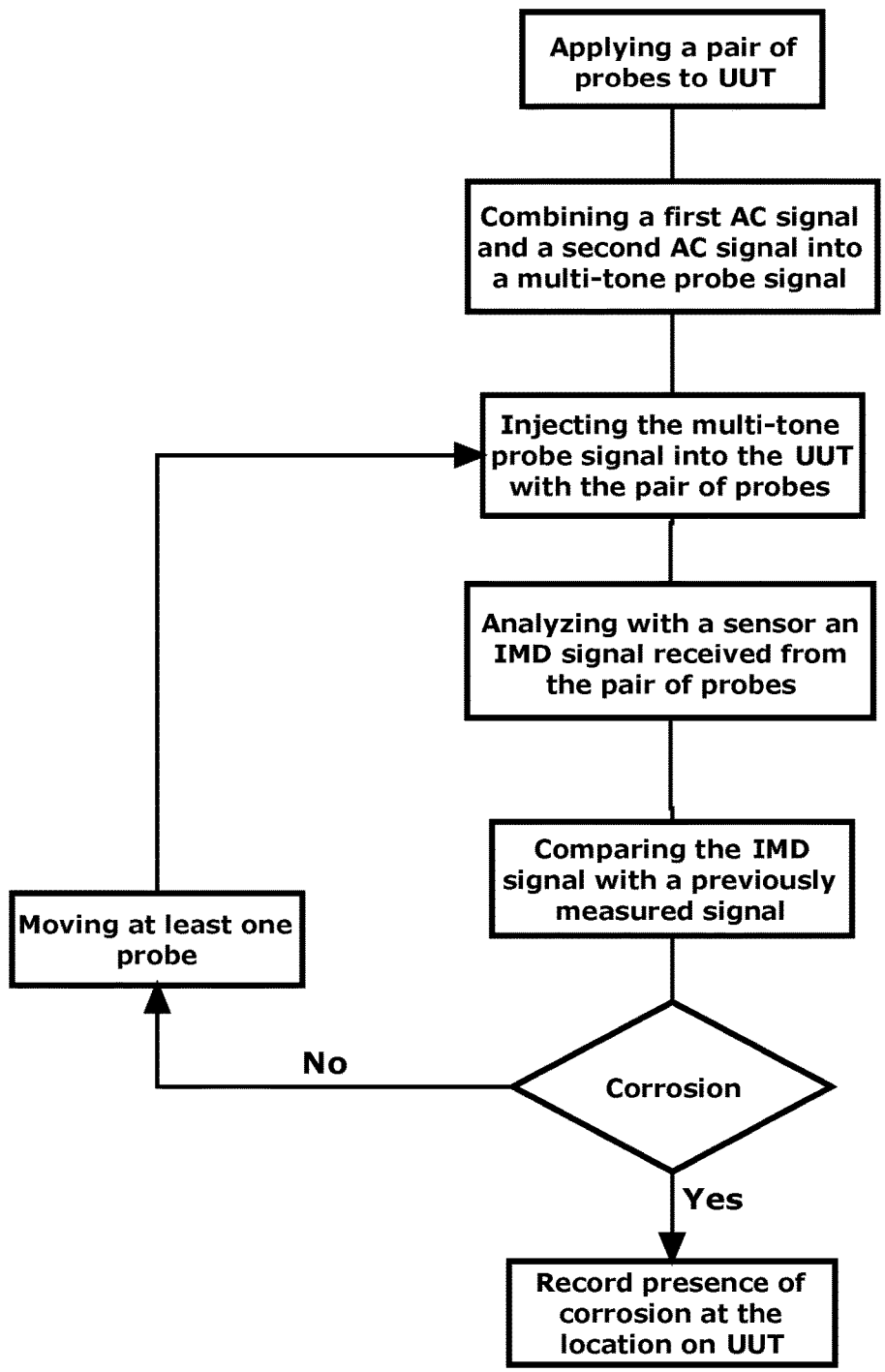
FIG. 2 is a flow chart of a method for detecting corrosion in a unit under test in accordance with this disclosure.

Disclosed is a system and method for detecting metal corrosion using Passive Inter-Modulation (PIM) generated by multi-tone radio signals flowing through galvanic corrosion junctions. More specifically, disclosed is a system and method that: (1) uses the PIM effect to detect and locate corrosion; (2) determines PIM signatures of various metal combinations producing corrosion; and (3) uses a system for easily applying the PIM effect and detecting/locating corrosion.

This disclosure makes use of two principles, passive intermodulation ("PIM") and intermodulation distortion ("IMD"). Passive Intermodulation (PIM) is an unwanted distortion in radio frequency waves generated by the non-linear mixing of two or more frequencies in passive devices such as antennas, connectors, coaxial cables, conductors, and the like. This mixing produces additional unwanted signals that can create interference and degradation in the quality of alternating current ("AC") signals.

PIM effects have long been known, most popularly as "rusty bolt" interference onboard ships that are generated by multiple high power HF transmitters generating circulating currents passing through rusty steel joints. The recent growth in the cellular industry and the use of multi-carrier waveforms has revealed a microwave tower-top environment at least as bad as the shipboard environment. So, this phenomenon has become more troublesome as spectrum density increases.

IMD describes a ratio (in dB) between the power of fundamental tones and distortion products. When one or more AC signals are applied to a "black box" input, then the output can be computed by doing a power-series expansion of the input signals and "black box" transfer function to obtain the output signal characteristics. If the "black box" is a linear system, only the original signals will appear at the output, possibly altered in time or amplitude. If the "black box" is a non-linear system, additional spectral components ("products" of the non-linearity) from PIM will be generated by the non-linearity and be present at the output. This disclosure makes use of the IMD products of non-linear systems.

More specifically, the relationship defining the frequencies of IMD products produced by a non-linear network is:

$$FIMD = \pm(N1*F1) \pm (N2*F2) \pm (N3*F3) \pm (N4*F4) \pm (N5*F5) \pm \ldots$$

where:
FIMD=Uniquely-generated signal at frequency FIMD
Fi=An AC signal frequency
Nj=Harmonic integer coefficient for each AC signal, varies 1 to highest value of importance
Order=Order of intermodulation (IM) product=|N1|+|N2|+|N3|+|N4|+|N5|+ . . . .
=Sum of all [absolute value] harmonic coefficients generating a specific IM product If i=1 AC signal, for example, then the non-linear system will output the original signal F1 and its entire harmonic (integer multiple) products, i.e., 2*F1, 3*F1, 4*F1, 5*F1 . . . .

With two AC signals (for illustration, $F_1=5$, $F_2=6$) applied to a non-linear network (with the expansion limited to third order (e.g., $|N_1|+|N_2|=3$) intermodulation products) each coefficient can assume a value of 0, 1, 2 or 3. The non-linear network output will consist of the following IM3 (shorthand for third order IMD products) shown in form $F_{IMD} = \pm(N_1*F_1) \pm (N_2*F_2)$:

Coefficients 0, 3:  0*5+   −0*5+   0*5−    −0*5−
                    3*6=18  3*6=18  3*6=−18 3*6=−18

Coefficients 1, 2:  1*5+   −1*5+   1*5−    −1*5−
                    2*6=17  2*6=7   2*6=−7  2*6=−19

Coefficients 2, 1:  2*5+   −2*5+   2*5−    −2*5−
                    1*6=16  1*6=−4  1*6=4   1*6=−16

Coefficients 3, 0:  3*5+   −3*5+   3*5−    −3*5−
                    0*6=15  0*6=−15 0*6=15  0*6=−21

Thus, the third order products are at frequencies of 4, 5, 6, 7 and 15, 16, 17, 18 (negative frequencies are discarded as they have no physical significance).

This demonstrates one key principle: the number of precisely calculable IMD product frequencies increases exponentially with order and number of signals, and a cell tower with hundreds of simultaneous signals generates a very dense and damaging self-interference spectrum.

Any metal (or other conductive material) object lying within the electromagnetic field of a radiating antenna will have a signal power (typically called "circulating current") induced in it by the antenna field. These parasitic pieces of metal act as antennas that each siphon off a small portion of the radiated antenna power. The amount of current induced is a function of the radiating antenna power and distance, and the shape and electrical properties of the metal object. The current induced in a parasitic piece of metal then generates and reradiates its own electromagnetic field, which will be of a generally random phase and amplitude relationship to the original radiating antenna. PIM and "rusty bolt" effects are generated when there is a non-linearity in the current flow path in the parasitic piece of metal, which causes both the original signals and IMD products to be reradiated.

This disclosure teaches directly injecting a probe signal through direct physical contact with a unit under test ("UUT"), which is also referred to as "injection" throughout this disclosure, to induce circulating currents in the suspect area of corrosion. The emission of IMD products of the circulating currents in the area of corrosion can be sensed by the same pair of probes and precisely located, ideally down to ¼ inch resolution.

FIG. 1 shows a corrosion detection system 100 comprising of a pair of probes 102 for directly injecting current through physical contact with a unit under test (UUT) 200. Two sharp mechanical contacting points on pair of probes 102 are physically applied on UUT 200 to directly inject a two-tone current probe signal to UUT 200. Circulating currents will flow on the outside surface of UUT 200 in the path of least resistance from one probe to the other probe due to shielding effects of metal and the skin effect where higher frequency currents increasingly flow on a thinning outside layer of a conductor. The current induced in UUT 200 between pair of probes 102 in the presence of the localized corrosion generates and reradiates its own PIM circulating currents and electromagnetic field, which will be of a generally random phase and amplitude relationship to the injected signals. The specific corrosion location can be isolated by moving pair of probes 102 about UUT 200 to cause currents to flow across a region of interest in UUT 200. The corrosion most likely will lie between the two application points of pair of probes 102 where a measured intermodulation distortion ("IMD") product is the strongest. Corrosion detection system 100 detects and analyzes the IMD signal that is received from pair of probes 102 probing UUT 200. It is significant that the same pair of probes 102 both inject the probe signal and sense the IMD signal, and that there is a continuous path of travel through a physical medium (i.e. the circuit and the UUT) of the probe signal and the return, IMD signal.

More specifically, corrosion detection system 100 comprises of a first signal generator 104 for generating a first AC current signal and a second signal generator 106 for generating a second AC current signal. First signal generator 104 and second signal generator 106 are each capable of generating alternating current ("AC") signals in the range of 1 HZ to 26 gHz (and any value in between). AC signals of greater frequency can be used. First signal generator 104 and second signal generator 106 generate current signals of distinct frequencies. These frequencies can be few Hertz to tens of Mega Hertz apart with the understanding that the precise frequency spacing will be selected to optimize the power of the IMD signal for a given type of corrosion and structure being analyzed.

A first combiner 108 mixes the first AC current signal and the second AC current signal. First combiner 108 can be a commercial off-the-shelf wideband combiner that provides a minimum of 20 db (100:1) of isolation between the two signals by virtue of its phase cancellation and balance. A balun transformer that converts a balanced signal to an unbalanced signal can be used. Combiner 108 mixes first AC current signal and second AC current signal received at the respective input ports and combines them into a probe signal at the output for applying to UUT 200. A first attenuator 110 is coupled between first signal generator 104 and first combiner 108 and a second attenuator 112 is coupled between second signal generator 106 and first combiner 108. Each first attenuator 110 and second attenuator 112 limit any back feeding of power from one of first signal generator 104 and second signal generator 106 to the other and limits the generation of any IMD products in the source circuitry.

A receiver 114 receives analyzes an IMD signal created from the probe signal in UUT. Receiver 114 can be a spectrum analyzer or a wide tuning range radio receiver, with receive capability commensurate with the probe signals and expected IMD products.

A second combiner 116 is coupled to first combiner 108. Second combiner is similar in operation to first combiner 108. Second combiner 116 can be a commercial off-the-shelf wideband combiner that provides a minimum 20 db (100:1) of isolation between input signals by virtue of its phase cancellation and balance. Second combiner 116 receives the probe signal from first combiner 108 and also receives the IMD signal from pair of probes 102 probing UUT 200. A third attenuator 118 is coupled between second combiner 116 and receiver 114 to protect receiver 114 from the probe signal overloading the instrument. Second combiner 116 importantly prevents mixing of the probe signal and the IMD signal to allow for both the injection of the probe signal and the sensing of the IMD signal on a single pair of probes, in this regard second combiner 116 maintains signal-separation between the probe signal and the IMD signal.

A step-down transformer 120 is coupled between pair of probes 102 and second combiner 116 for stepping down an approximately fifty ohm impedance on a second combiner side of step-down transformer 120 to a lower impedance on the two probes side of step-down transformer 120. The stepping down of the impedance is commensurate with the expected low impedance of UUT 200 comprising of a large metal structure. Impedance matching minimizes the probe power required and maximizes the power of the IMD signal from pair of probes 102 probing UUT 200. Pair of probes 102 can be connected to the two leads of the port for step-down transformer 120.

The utility of corrosion detection system 100 can be enhanced with an empirical set of rules for the signal frequencies of the IMD signal and power levels necessary to locate corrosion. This can be done with a library of measurements from a variety of corroded metal parts to locate previously identified corrosion and by applying a wide range of probe signals to varying locations on the parts and recording IMD signals. These measurements can be compared with an un-corroded equivalent part for each for comparison. More specifically, the widest possible range of experimental data can be recorded while varying the probe signal power and frequency and injection points versus the type of metal and corrosion.

A processor 122 is provided to compare the IMD signal from UUT 200 with a library 124 of previous measurements. Processor 122 can include multiple processors, multiple cores, or reside on a single processor. Processor 122 can be connected to receiver 114 by any number of wired or wireless connections using any number of transmission protocols. Processor can also be connected to an internal or external data storage repository where library 124 is stored. Processor 122 can alert the operator of the presence of corrosion in UUT 200 or record the presence of corrosion for later analysis.

A method 300 for detecting corrosion in UUT 200 is also disclosed. Method 300 begins by applying pair of probes 102 to UUT 200. Method continues by combining the first AC signal from first signal generator 104 and second AC signal from second signal generator 106 into a probe signal. First AC signal and second AC signal are of a distinct frequency so the probe signal is a multi-tone probe signal. Method 300 continues with injecting the multi-tone probe signal to UUT 200 with pair of probes 102. Thereafter, method 300 continues with analyzing with receiver 114 the IMD signal received from pair of probes 102, and then comparing the IMD signal with a previously measured signal.

Method 300 continues with a decision on whether corrosion in UUT 200 is detected. If yes, the method continues with alerting the operator and recording the presence of corrosion at the location on UUT 200. If no, the method continues with the operator moving at least one probe of the pair of probes to another location and continuing method 300 with injecting the multi-tone probe signal to UUT 200 with pair of probes 102.

Corrosion detection system 200 and method 300 for detecting corrosion can be modified for detecting corrosion in aluminum. Unlike metal components, corrosion on aluminum manifests itself as aluminum oxide. Aluminum oxide is an insulator, if present the junction will appear as high impedance to low frequency AC signals because the junction has become a pair of capacitor plates rather than a low-resistance metal-to-metal conducting path. That high impedance will results in a low signal current passing through it. The "capacitor" will appear as low impedance to high frequency signals, allowing strong currents to circulate and providing no useful information.

The key to the aluminum corrosion detection is having a new structure "fingerprint" that specifies sets of measurement points and the measured impedance between those two points for a new aluminum metal structure known to be corrosion-free. Later maintenance records can accumulate comparative measurements over the life of the structure. Such measurements can be stored in library 124, as described above.

Reference may also have been made throughout this disclosure to "one embodiment," "an embodiment," or "embodiments" meaning that a particular described feature, structure, or characteristic is included in at least one embodiment of the present invention. Thus, usage of such phrases may refer to more than just one embodiment. Furthermore, the described features, structures, or characteristics may be combined in any suitable manner in one or more embodiments.

While the present invention has been particularly shown and described with reference to exemplary embodiments thereof, it should be understood by those of ordinary skill in the art that various changes, substitutions and alterations can be made herein without departing from the spirit and scope of the invention as embodied by the appended claims and their equivalents.

What is claimed is:

1. A system for detecting corrosion in a unit under test, the system comprising:
   a first signal generator for generating a first AC current signal;
   a second signal generator for generating a second AC current signal;
   a first combiner coupled to the first signal generator and the second signal generator for combining the first AC current signal and the second AC current signal into a probe signal for applying to the unit under test;
   a second combiner comprising a first port coupled to the first combiner for receiving the probe signal and a second port;
   two probes coupled to the second combiner each of the two probes configured for receiving the probe signal and applying the probe signal through direct physical contact to one of two distinct locations on the unit under test for inducing circulating currents between the two distinct locations on the unit under test and sensing the intermodulation distortion of the circulating currents between the two distinct locations where the two probes are applied to the unit under test; and
a receiver coupled to the second port of the second combiner for detecting intermodulation distortion between the two probes when they are applied simultaneously to the two distinct locations on the unit under test.

2. The system of claim 1, and further comprising a step-down transformer coupled between the two probes and the second combiner for stepping down an approximately fifty ohm impedance on a second combiner side of the step-down transformer to a lower impedance on the two probes side of the step-down transformer.

3. The system of claim 2, and further comprising a first attenuator coupled between the first signal generator and the first combiner and a second attenuator coupled between the second signal generator and the first combiner, wherein the first attenuator and the second attenuator limit an amount of back feeding of power from one of the first signal generator and the second signal generator to the other.

4. The system of claim 3, and further comprising a third attenuator coupled between the second combiner and the receiver to protect the receiver from the probe signal.

5. The system of claim 1, wherein the first AC current signal has a frequency that is distinct from a frequency of the second AC current signal.

6. The system of claim 1, and further comprising a library of measurement tests on material similar to the unit under test and a comparator for comparing the intermodulation distortion in the unit under test with measurement tests on the material similar to the unit under test from the library for determining an amount of corrosion in the unit under test.

7. The system of claim 1, wherein the probe signal travels in a continuous path of travel through a physical medium, and wherein the two probes inject the probe signal to the UUT and sense the intermodulation distortion.

8. A method for detecting corrosion in a unit under test (UUT), the method comprising:
injecting a multi-tone probe signal with a pair of probes at two distinct locations to the UUT and inducing circulating currents between the two distinct locations of the UUT;
analyzing with a receiver intermodulation distortion of the circulating currents between the two distinct locations of the UUT in an IMD signal received from the pair of probes that are simultaneously in contact with the UUT at the two distinct locations, wherein the receiver comprises an input port;
maintaining signal-separation between the multi-tone probe signal and the IMD signal with a combiner coupled to the pair of probes and comprising a first port coupled to the input port of the receiver;
comparing the IMD signal with a previously measured signal to determine a presence of corrosion in the UUT; and
moving at least one probe of the pair of probes to another location on the UUT when lack of corrosion is detected.

9. The method of claim 8, wherein the previously measured signal is representative of an intermodulation distortion signal from a part similar to the UUT with an area of corrosion.

10. The method of claim 8, wherein the previously measured signal is representative of an intermodulation distortion signal from a part similar to the UUT without corrosion.

11. The method of claim 8, and further comprising combining a first AC current signal and a second AC current signal into the multi-tone probe signal.

12. A system for detecting corrosion in a unit under test ("UUT"), the system comprising:
a pair of probes for injecting in two distinct locations a two-tone probe signal to a UUT for inducing circulating currents on the UUT between the pair of probes and sensing intermodulation distortion of the circulating currents between the pair of probes in an IMD signal;
a source providing the two-tone probe signal to the pair of probes;
a first combiner coupled to the source and comprising a first output port;
a second combiner coupled to the pair of probes and comprising a first port that is coupled to the first output port of the first combiner and a second port, wherein the second combiner maintains signal-separation between the probe signal and the IMD signal; and
a receiver coupled to the second port of the second combiner for analyzing the IMD signal while the pair of probes are simultaneously in contact with the UUT.

13. The system of claim 12, and further comprising a continuous path of travel of the probe signal and the IMD signal through a physical medium.

14. The system of claim 13, wherein the source further comprises of a first signal generator for generating a first AC current signal and a second signal generator for generating a second AC current signal, wherein the first AC current signal has a frequency that is distinct from a frequency of the second AC current signal.

15. The system of claim 14, wherein the first combiner is coupled to the first signal generator and the second signal generator for combining the first AC current signal and the second AC current signal into the probe signal.

16. The system of claim 14, wherein the second combiner receives the probe signal, and further comprising a step-down transformer coupled between the two probes and the second combiner for stepping down an approximately fifty ohm impedance on a second combiner side of the step-down transformer to a lower impedance on the two probes side of the step-down transformer.

* * * * *